(12) United States Patent
Sand et al.

(10) Patent No.: US 9,693,873 B1
(45) Date of Patent: Jul. 4, 2017

(54) IN VITRO PRODUCTION OF BONE-LIKE MATERIAL

(75) Inventors: Theodore Sand, Austin, TX (US); Matthew Murphy, Austin, TX (US); Kevin Dunworth, Dripping Springs, TX (US)

(73) Assignee: SpineSmith Partners, L.P., Austin, TX (US)

( * ) Notice: Subject to any disclaimer, the term of this patent is extended or adjusted under 35 U.S.C. 154(b) by 275 days.

(21) Appl. No.: 13/594,835

(22) Filed: Aug. 26, 2012

Related U.S. Application Data

(60) Provisional application No. 61/575,713, filed on Aug. 26, 2011.

(51) Int. Cl.
*A61F 2/44* (2006.01)
*C12N 5/077* (2010.01)

(52) U.S. Cl.
CPC .......... *A61F 2/4455* (2013.01); *C12N 5/0654* (2013.01)

(58) Field of Classification Search
CPC ........... A61F 2/4455; A61F 2002/2835; A61F 2002/2817; A61K 35/12; A61K 35/32
USPC ............. 606/246–249; 623/17.11–17.16; 424/93.7, 548
See application file for complete search history.

(56) References Cited

U.S. PATENT DOCUMENTS

| | | | |
|---|---|---|---|
| 7,771,716 B2 * | 8/2010 | Hedrick | A61L 27/3834 424/93.7 |
| 2011/0262486 A1 * | 10/2011 | Tsai | A61K 33/24 424/400 |

* cited by examiner

*Primary Examiner* — Ellen C Hammond
*Assistant Examiner* — Christina Negrellirodrigue
(74) *Attorney, Agent, or Firm* — Winstead PC

(57) ABSTRACT

Embodiments of the invention is directed to methods of forming a bone-like material, by placing a matrix into a culture container, adding cells to the matrix, placing the tissue-cell construct into the culturing environment and incubating the construct under appropriate conditions for the time required to produce an amount of bone-like material of sufficient volume to be harvested for further processing. Other embodiments of the invention are directed to the use of the bone-like material formed by methods of the invention in implantation procedures.

20 Claims, 1 Drawing Sheet

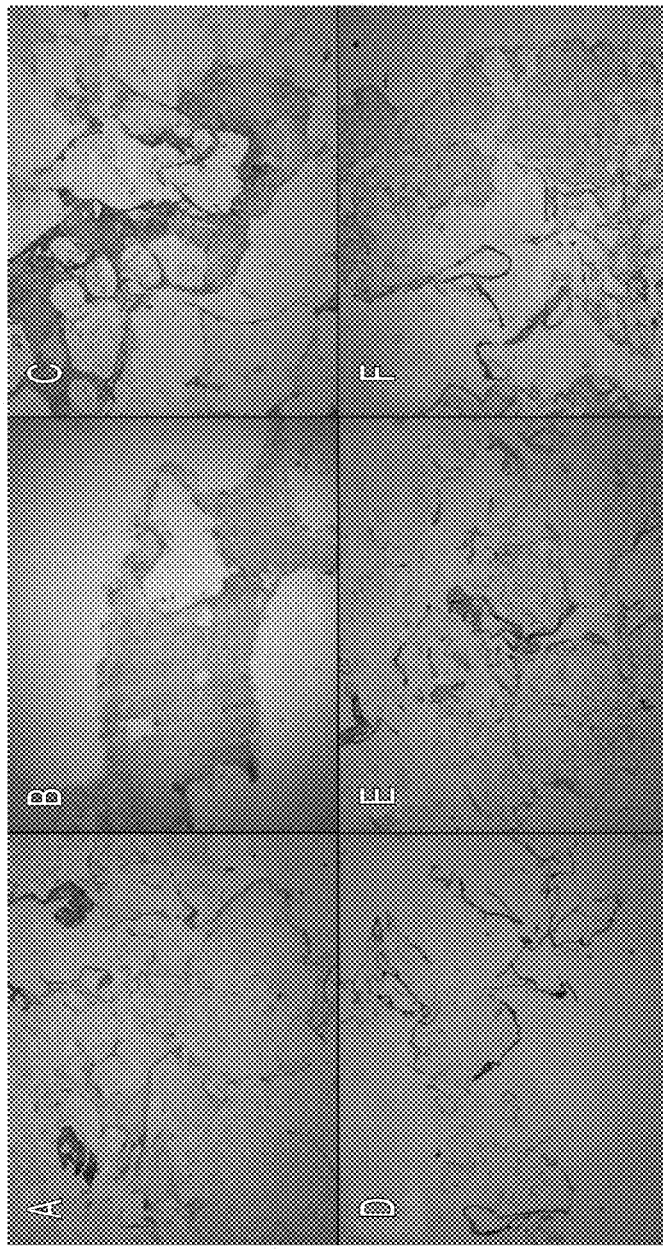

IN VITRO PRODUCTION OF BONE-LIKE MATERIAL

CROSS-REFERENCES TO RELATED APPLICATIONS

This Application claims the benefit under 35 U.S.C. §119(e) of U.S. Provisional Patent Application Ser. No. 61/575,713 filed Aug. 26, 2011, which is incorporated herein by reference in its entirety as if fully set forth herein.

FIELD OF THE INVENTION

Embodiments of the invention are directed to the in vitro production of a bone-like material that is biomechanically sound enough to provide stability in a fusion when used in any scenario where a need for bone tissue supplementation exists.

BACKGROUND OF THE INVENTION

A variety of materials have been used as scaffolds or matrices for supporting cells in various cell augmentation procedures. However, most studies are concerned with the creation of "functional" bone (i.e., so-called neocortical bone) in the host animal or patient. It appears that, to date, there has been no reference related to the creation of a bone-like material in vitro that is suitable for implantation in a spinal fusion procedure. A need for bone tissue supplementation exists in a wide range of clinical conditions involving surgical reconstruction following trauma or other pathological conditions in limbs and spine.

The amount and purpose of bone supplementation determines the origin of the used tissue, i.e. for bone inductive purposes, a supplementation of fresh autologous cancellous bone that contains cellular, mineral and humeral components, is required and usually is taken from a non-involved body site, and a material for bone conductive-support purposes might require either autografts or allografts. Both solutions for bone supplementation bear potential serious side effects and complications. Therefore, a possibility for in vitro generation of sufficient amount of autologous bone for inductive and conductive purposes should resolve these difficulties and complications.

SUMMARY OF THE INVENTION

An embodiment of the invention is directed to a method of forming a bone-like material, comprising: placing a matrix into a culture container, adding cells to the matrix, placing the tissue-cell construct into the culturing environment and incubating the construct under appropriate conditions for the time required to produce an amount of bone-like material of sufficient volume to be harvested for further processing.

Other embodiments of the invention are directed to the use of the bone-like material formed by methods of the invention in implantation procedures.

BRIEF DESCRIPTION OF THE DRAWINGS

The FIGURE shows Goldner's Trichrome stains for histological sections of bone-like materials synthesized in standard (A, B, C) or osteogenic media (D, E, F) for 7 (A, D), 14 (B, E), or 21 days (C, F), in accordance with embodiments of the invention.

DESCRIPTION OF EXEMPLARY EMBODIMENTS

As used herein, the terms matrix and scaffold and their plural forms are used interchangeably.

An embodiment of the invention pertains to the in vitro production of a bone-like material that is biomechanically sound enough to provide stability when used in any scenario where a need for bone tissue supplementation exists. Examples of such scenarios include, without limitation, intervertebral implants, or as a plate for bridging between adjacent vertebrae. The composition of the bone-like material is such that it will support osteogenic growth of cell-augmented matrices used to supplement bone tissue. Osteogenic growth leads to greater stabilization of the pathology, less need for revision due to loosening or implant migration and better integration of the implant with the surrounding tissue.

In an embodiment of the invention, the bone-like material is created in an in vitro environment and resembles the bone-like material observed in bone biopsy samples obtained from patients who have experienced a cell-augmented fusion procedure involving the use of a patient's own cells placed on a matrix and placed in the lateral gutters and/or in the cavity of an interbody implant. In certain embodiments of the invention, the matrix that can be used are cancellous chips (a donor-derived material available commercially).

The present invention overcomes the problems in the art by providing for a bone-like material/composition, such composition having the ability to bind to a component of the extracellular matrix of the host tissue upon implantation. Upon implantation, the bone-like material/composition allows the implant to integrate with the extra-cellular matrix components of the host tissue in a short period of time.

In an embodiment of the invention, the bone-like material bonds with collagen. Thus, any tissue that contains collagen in its extracellular matrix is a candidate for implantation of the composition. In a preferred embodiment, the composition is suitable for implantation into a mammal, to treat, repair or replace defects and/or injury to musculoskeletal tissue including, but not limited to, bone, tendon, ligaments, cartilage and the discs of the spine.

An embodiment of the invention is a bone-like material having shared characteristics of both bone and cartilage. The material is synthesized by multi-potent stromal or progenitor cells, sometimes referred to as mesenchymal stem cells (MSCs) on a substrate, scaffold, or matrix consisting of calcium phosphates and/or orthopedic proteins. The calcium phosphates may be natural (e.g. allogenic bone fragments) or synthetic (hydroxyapatite, a tricalcium phosphate, carbonate apatite, etc.). The orthopedic proteins may be collagen (derived from human bone—allogenic bone fragments or demineralized bone—or from animals [e.g. bovine or porcine collagen type I or type II]), fibrinogen (recombinant or derived from human or mammalian blood, bone marrow, or plasma), glycosaminoglycans (GAG, e.g. hyaluronic acid), and/or aggrecan.

In accordance with certain embodiments of the invention, the scaffolds or matrices that are contemplated for use in producing an implantable bone-like device include, but are not limited to, pure tri-calcium phosphate, pure hydroxyapatite, demineralized bone matrix, bi- or multi-phasic matrices (combinations of tri-calcium phosphate and hydroxyapatite in various ratios; combinations with collagen; etc.) and polymeric matrices like poly(L-lactide-coglycolide), poly(e-caprolactone) or combination thereof, either with or without other scaffold materials.

In an embodiment of the invention, the in vitro environment supports the attachment and viability of cells that are responsible for the remodeling of the selected matrix. Such in vitro environments involve the use of an appropriate tissue culture fluid to sustain cell viability. Examples of tissue culture fluids used in embodiments of the invention include, without limitation, fetal bovine serum or a medium that is xeno-protein free or a medium that is completely defined (i.e., that doesn't contain serum or non-human proteins). Media is commercially available for producing allogeneic cells for therapeutic use (e.g., Prochymal, Osiris), and such media would be appropriate for use as a tissue culture fluid in embodiments of the invention.

In certain embodiments of the invention, the in vitro environment supports the temperature and gas exchange requirements of cells placed into tissue culture (i.e., maintenance at 37° C.). The optimal level of $O_2$ varies and can be optimized for given compositions, but could include levels considered as hypoxic (i.e., 0.1 to 1.0% v/v). Other conditions can also be optimized, including but not limited to the use of a perfusion approach, in which the implants are continuously bathed in culture fluid or static culture, in which the implant is left in a chamber and medium is exchanged manually.

In accordance with an embodiment of the invention, the method of producing a bone-like implant device in vitro comprises, placing the selected matrix into a culture container, adding the cells of interest (such as those derived from cultured cells lines obtained from a bone marrow aspirate or from cells cultured from an adipose-derived cell culture) to the matrix, placing the tissue-cell construct into the culturing environment and incubating the construct under appropriate conditions for the time required to produce an amount of bone-like material of sufficient volume to be harvested for further processing into an implantable device. Variations in the production process include creating sheets of bone-like material that later can be laminated together to produce an implant of the desired geometry or the addition of bone-inducing growth factors into the culture environment at periodic intervals to promote continued secretion of bone-like material associated with the remodeling of the matrix. Additional variations include periodic addition of fresh aliquots of cultured cells or the use of low passage number cell preparations obtained from qualified donors, including bone marrow cultured cells as well as adipose-derived cultured cells. Processing of the bone-like material produced could be expedited if matrix-cell constructs were placed in forms or other non-reactive containers that limit the growth of the bone-like material to certain shapes or thicknesses.

Once a bone-like material "plug" has been obtained, the cells present in the material need to be removed, before the formed bone-like material can be used for any practical purpose. This process is called "de-cellularization" and is well known in the tissue engineering art. However, use of acids and certain temperature treatments must be avoided in order to ensure the integrity and biomechanical strength of the "plug". Once the bone-like material has been de-cellularized, the material can be formed into an implantable device. While creation of an implantable device is the primary focus of the invention, if the de-cellularized material is rendered into a particulate form, the material can be used as a matrix in treating non-unions of long bones, spinal fusions and other bony-growth dependent therapies.

The bone-like material may be de-cellularized by methods including freeze-thaw cycling and/or washing with detergents or solvents in order to preserve the biological activity. The de-cellularized material may be sterilized by gas (e.g. ethylene oxide). The treated material may retain properties that are bone-like including mineralization, collagens (type I and X), and/or stiffness and compressive modulus similar to bone. The treated material may retain properties that are cartilage-like including collagens (type II, IX, X, and XI), hyaluronic acid, and/or aggrecan and compressive and tensile moduli similar to cartilage. The treated material may retain intermediate properties that are fibrocartilage-like including collagens (type I and X), hyaluronic acid, and/or mineralization. As a consequence, the treated material will be suitable for use in a variety of pathologies, including being implanted at the site of a bone void (e.g. osteosarcoma resection, trauma, spinal fusion) or being implanted as cartilage replacement (e.g. intervertebral disc, knee meniscus).

A key distinction between the claimed invention and the current practice in treating fusions involving cell-augmentation is that the disclosed invention does not contain live cells at the time of implantation. However, the nature of the material is such that it will be osteo-supportive and will have sufficient mechanical strength to provide sufficient stabilization in a fusion procedure such that additional, traditional hardware or an interbody device is not required. An important advantage to the use of devices and hardware made in the proposed method which mimics the bone-like material observed in bone biopsy samples obtained from patients treated with cell-augmented matrices in a fusion procedure is that the material is osteogenic, osteoconductive and osteoinductive, thereby supporting a more rapid stabilization of the spinal pathology and contributing to a reduction in back pain more rapidly and for a longer duration than current procedures involving standard materials and hardware.

Embodiments of the invention accelerate the time for bone, cartilage, or pseudo-bone formation in vivo after implantation, by influencing MSCs (either co-delivered with the material or recruited endogenous cells) with its biological and biochemical properties. Polymers with pre-cultured extracellular matrix (ECM) can induce bone formation by fresh MSCs.

In an embodiment of the claimed invention, donor MSCs, which may be derived from bone marrow, adipose/stromal vascular tissue, bone, dermis, muscle, placenta, umbilical cord, and other tissues, are combined with the scaffold. In certain embodiments, the combination is supplemented with an adhesive or thickening agent such as plasma, platelet-poor plasma (PPP), platelet-rich plasma (PRP), serum, blood, bone marrow, fibrin glue, proteins (e.g. collagen, fibrinogen, thrombin), carbohydrates (e.g. carboxymethylcellulose), proteoglycan (e.g. aggrecan), glycosaminoglycan (GAG, e.g. hyaluronic acid), or synthetic polymers (e.g. polyethylene glycol).

The prepared composite is cultured in vitro for a period of time ranging up to 60 days. The cell culture medium may be (1) standard media with fetal bovine serum, human serum, human PRP, or human platelet lysate and glucose, glutamine, and/or sodium pyruvate; (2) osteogenic media containing dexamethasone, ascorbic acid, ascorbate-2-phosphate, and/or bone morphogenetic proteins (e.g. recombinant human or mammalian BMP-2 or BMP-7); (3) chondrogenic media containing transforming growth factor beta (e.g. human or mammalian TGF-b1, TGF-b2, TGF-b3), bone morphogenetic proteins (e.g. human or mammalian BMP-2, BMP-6, BMP-7 or BMP-9), platelet-derived growth factor (PDGF), dexamethasone, ascorbic acid, ascorbate-2-phosphate, insulin, transferrin, and/or insulin-transferrin-selenium (ITS); or (4) a combination thereof. Osteogenic (bone-like-forming) or chondrogenic (cartilage-like-forming) induction may be supplemented by mechanical induction of the material by pulsatile medium flow, continuous medium flow, sheer stresses within a bioreactor, mechanical compression, tension, and/or torsion.

The bone-like material may be de-cellularized by methods including freeze-thaw cycling and/or washing with detergents or solvents in order to preserve the biological activity. The de-cellularized material may be sterilized by gas (e.g. ethylene oxide). The treated material may retain properties that are bone-like including mineralization, collagens (type I and X), and/or stiffness and compressive modulus similar to bone. The treated material may retain properties that are cartilage-like including collagens (type II, IX, X, and XI), hyaluronic acid, and/or aggrecan and compressive and tensile moduli similar to cartilage. The treated material may retain intermediate properties that are fibrocartilage-like including collagens (type I and X), hyaluronic acid, and/or mineralization. As a consequence, the treated material will be suitable for use in a variety of pathologies, including being implanted at the site of a bone void (e.g. osteosarcoma resection, trauma, spinal fusion) or being implanted as cartilage replacement (e.g. intervertebral disc, knee meniscus).

An advantage to using the treated material that retains cartilage-like properties in the treatment of bone defects is that the treated material will be subjected to the natural, in vivo process of endochondral ossification, wherein biomechanical forces promote the remodeling of cartilage or fibrocartilage tissue into bone. Another application for the bone-like material of the claimed invention is spinal fusion, where bone is grown to replace a cartilaginous intervertebral disc. The bone-like material may be remodeled to form mature bone or a softer pseudo-bone based upon the biomechanical environment and the normal loads experienced at that level in the spine. It is possible to achieve a successful therapeutic relief of pain by removing the patient's disc and inserting an implant of bone chips, cells and growth factors, which over the course of time results in the creation of a spinal fusion mass. These spinal fusion masses have been examined histological and found in some cases to demonstrate bone-like histological features, but are not considered to be "mature bone". The bone-like material of the claimed invention is similar to this fusion mass tissue and may accelerate the fusion process as a better implantation material. A secondary advantage of these materials is the potential avoidance of adjacent disc disease or syndrome, where disc-replacing fusion masses or implants are too rigid and do not conduct biomechanical loads naturally between adjacent vertebral bodies. This stress-shielding may be circumvented by the implantation of the softer bone-like material as a disc surrogate, softer than bone but stiffer than normal cartilage, resulting in a soft fusion that will not cause degeneration of discs at adjacent levels.

An embodiment of the invention is directed to a method for in vitro bone generation. In this method bone matrix generating cells, osteoblasts, were seeded on an inorganic supporting matrix (porous calcium triphosphate) allowing exposure of cells to osteogenic medium. The source for osteoblasts is typically mesenchymal precursor cells originated from disposable human cancellous bone samples. The osteoblasts are initially grown as explant primary cultures, in special bone inductive medium and presented osteoblastic characteristics, e.g. osteopontin and osteocalcin expression, and cellular alkaline phosphatase activity.

An example of the preparation of the bone-like materials of the invention in vitro is set forth below. These materials exhibit histological properties that are very similar to biopsies of spinal fusion masses. Briefly, hydroxyapatite and beta-tricalcium phosphate particles were combined with bone marrow or adipose-derived MSCs, human plasma, and thrombin. These materials were cultured in vitro for 7, 14, or 21 days in standard or osteogenic media. (1) Goldner's Trichrome and (2) Hematoxylin and Eosin staining of 5 μm histological sections revealed structural morphology and biochemical structure similar to spinal fusion masses (Goldner's Trichrome stains shown in the FIGURE). Dense extracellular matrix was observed in the material beyond 7 days in standard media (A-7 days; B-14 days; C-21 days), while osteogenic media induced osteoblastic activity and mineralization (D-7 days; E-14 days; F-21 days).

Thus, the interaction of the cellular, inorganic and mechanical components in the described in vitro experiment rapidly generated bone tissue that may be kept viable in vitro for a significant time period, i.e., up to 21 days.

What is claimed is:

1. A method of forming a bone-like material, comprising:
   placing a matrix comprising calcium phosphate into a culture container;
   adding mesenchymal stem cells to the matrix;
   placing the matrix-cell construct into a culturing environment and incubating the construct under appropriate conditions for a time required to produce an amount of bone-like material of sufficient volume to be harvested for further processing.

2. The method of claim 1, further comprising de-cellularizing the bone-like material using freeze thaw cycling or washing with detergents and solvents.

3. The method of claim 2, further comprising forming the de-cellularized bone-like material into an implant.

4. The method of claim 3, wherein the implant is a spinal fusion implant.

5. The method of claim 1, wherein the matrix is tricalcium phosphate, hydroxyapatite, demineralized bone matrix, collagen or polymers.

6. The method of claim 1, wherein the calcium phosphate comprises allogenic bone fragments.

7. The method of claim 1, wherein the calcium phosphate comprises one or more of hydroxyapatite, tricalcium phosphate, and carbonate apatite.

8. The method of claim 1, wherein the matrix further comprises an orthopedic protein that comprises glycosaminoglycans or aggrecan.

9. A composition comprising:
   an implant and bone-like material, wherein the bone-like material is bound to the implant and has the ability to bind to a component of an extracellular matrix of a biological tissue, whereby the implant and the biological tissue become attached upon introduction of the composition to biological tissue; and
   wherein the bone-like material is formed by placing a matrix comprising calcium phosphate into a culture container, adding mesenchymal stem cells to the matrix, placing the tissue-cell construct into the culturing environment and incubating the construct under appropriate conditions for a time required to produce an amount of bone-like material.

10. The composition of claim 9, wherein the bone-like material is formed in vitro.

11. The composition of claim 9, wherein the implant is porous.

12. The composition of claim 9, wherein the implant allows for migration of the mesenchymal stem cells into the implant.

13. The composition of claim 9, wherein the implant comprises hydroxyapatite, tricalcium phosphate, fibrin or fibrinogen.

14. The composition of claim 9, further comprising a growth factor.

15. A method of using the composition of claim 9 for treatment, repair or replacement of musculoskeletal tissue, by implantation of the composition into a subject in need thereof.

16. The method of claim 15, wherein a subject receiving treatment is a mammal.

17. The method of claim 16, wherein the mammal is a human.

18. The composition of claim 9, wherein the calcium phosphate comprises allogenic bone fragments.

19. The composition of claim 9, wherein the calcium phosphate comprises one or more of hydroxyapatite, tricalcium phosphate, and carbonate apatite.

20. The composition of claim 9, wherein the matrix further comprises an orthopedic protein that comprises glycosaminoglycans or aggrecan.

\* \* \* \* \*